(12) United States Patent
Scheker et al.

(10) Patent No.: US 8,048,162 B2
(45) Date of Patent: Nov. 1, 2011

(54) LATERAL ELBOW PROSTHESIS—PROXIMAL RADIOULNAR JOINT

(75) Inventors: Luis Roman Scheker, Glenview, KY (US); Bryan Babb, Jeffersonville, IN (US)

(73) Assignee: Aptis Medical, LLC, Louisville, KY (US)

( * ) Notice: Subject to any disclaimer, the term of this patent is extended or adjusted under 35 U.S.C. 154(b) by 364 days.

(21) Appl. No.: 12/140,372

(22) Filed: Jun. 17, 2008

(65) Prior Publication Data

US 2011/0166663 A9 Jul. 7, 2011

Related U.S. Application Data

(63) Continuation-in-part of application No. 11/306,312, filed on Dec. 22, 2005, now Pat. No. 7,708,781, and a continuation of application No. PCT/US2006/062463, filed on Dec. 21, 2006.

(51) Int. Cl.
*A61F 2/38* (2006.01)

(52) U.S. Cl. .................................................. 623/20.11

(58) Field of Classification Search ..... 623/20.11–20.13
See application file for complete search history.

(56) References Cited

U.S. PATENT DOCUMENTS

| | | | |
|---|---|---|---|
| 3,875,594 A | 4/1975 | Swanson | |
| 4,106,128 A | 8/1978 | Greenwald et al. | |
| 4,158,893 A | 6/1979 | Swanson | |
| 4,164,793 A | 8/1979 | Swanson | |
| 4,178,640 A | 12/1979 | Buechler et al. | |
| 4,180,871 A | 1/1980 | Hamas | |
| 4,198,713 A | 4/1980 | Swanson | |
| 4,224,695 A * | 9/1980 | Grundei et al. | 623/20.12 |
| 4,229,841 A | 10/1980 | Youm | |
| 4,349,922 A | 9/1982 | Agee | |
| 4,784,661 A | 11/1988 | Beckenbaugh et al. | |
| 5,108,444 A | 4/1992 | Branemark | |
| 5,133,762 A | 7/1992 | Branemark | |
| 5,314,485 A | 5/1994 | Judet | |
| 5,326,364 A | 7/1994 | Clift, Jr. et al. | |
| 5,458,646 A | 10/1995 | Giachino et al. | |
| 5,507,821 A | 4/1996 | Sennwald et al. | |
| 5,702,470 A | 12/1997 | Menon | |
| 5,782,923 A | 7/1998 | Engelbrecht et al. | |
| 5,782,926 A | 7/1998 | Lamprecht | |
| 5,951,604 A | 9/1999 | Scheker | |
| 6,059,832 A | 5/2000 | Menon | |
| 6,221,073 B1 | 4/2001 | Weiss et al. | |
| 6,712,820 B2 | 3/2004 | Orbay | |

(Continued)

FOREIGN PATENT DOCUMENTS

EP 34 192 8/1981

(Continued)

OTHER PUBLICATIONS

CFV Wrist System, Biomet, Inc., Form No. Y-BMT-152/013190.

(Continued)

*Primary Examiner* — Bruce E Snow
(74) *Attorney, Agent, or Firm* — Camoriano and Associates; Theresa Fritz Camoriano; Guillermo Camoriano (57) ABSTRACT

A proximal radioulnar joint (lateral elbow) prosthesis includes an ulnar brace member to be secured to the outer surface of the ulna bone. The ulnar brace member defines a bearing surface for supporting the radius. The prosthesis may also include a radial brace member which cooperates with the ulnar brace member.

14 Claims, 8 Drawing Sheets

U.S. PATENT DOCUMENTS

2004/0220675 A1* 11/2004 Lewis et al. ............. 623/20.11
2008/0195217 A1* 8/2008 Scheker ................. 623/20.11

FOREIGN PATENT DOCUMENTS

| FR | 2660856 | | 10/1991 |
|---|---|---|---|
| GB | 2269752 | | 8/1993 |
| WO | WO 91/16017 | | 10/1991 |
| WO | WO 92/00709 | | 1/1992 |
| WO | WO 01/01892 | | 1/2001 |
| WO | WO 2004/066883 | | 8/2004 |
| WO | 2007073564 | * | 6/2007 |

OTHER PUBLICATIONS

'Clinical Mechanics of the Hand', Second Edition, 1993 by Mosby—Year Book, St. Louis, MO.

Silastic HP 100 Swanson Finger Joint Implant and Dow Corning Wright Swanson Finger Joint Grommet II Dow Corning Wright Catalog.

Sutter Implants for the Hand and Forearm, brochure by Sutter Corporation; 14 pages; dated Feb. 12, 1990.

The Journal of Bone and Joint Surgery, vol. 69-A, No. 7, Sep. 1987, Jayasanker Merton, MD, 'Total Wrist Replacement Using the Modified Volz Prosthesis'.

The Journal of Hand Surgery, vol. 10A No. 1, Hans Christoph Meuli, MD, et al.,. Jan. 1995, "Uncemented Total Wrist Arthroplasty", pp. 115-121, 802.

Mayo Clinic College of Medicine, 200 First Street SW, Rochester, MN 55905; Use of an Ulnar Head Endoprosthesis for treatment of an unstable distal ulnar resection . . . 2005.

Acurned, Acu-Loc Targeted Distal Radius System.

Hand Innovations, The Anatomical DVR Surgical Technique, from web site.

Kinetikos Medical Incorporated, Universal 2 Total Wrist Implant System, from web site.

Small Bone Innovations, uHead Ulnar Implant System, from web site.

Small Bone Innovations, Total Wrist Implant, from web site.

Stryker, Universal Distal Radius System, from web site.

Wright, Evolve Radial Head Plate, from web site.

Wright, Locon VLS Distal Radius System, from web site.

* cited by examiner

LATERAL ELBOW PROSTHESIS—PROXIMAL RADIOULNAR JOINT

This application is a continuation-in-part of U.S. patent application Ser. No. 11/306,312, filed Dec. 22, 2005 now U.S. Pat. No. 7,708,781, and is a continuation of PCT/US2006/062463, filed Dec. 21, 2006, both of which are hereby incorporated herein by reference.

BACKGROUND

Figure 1:
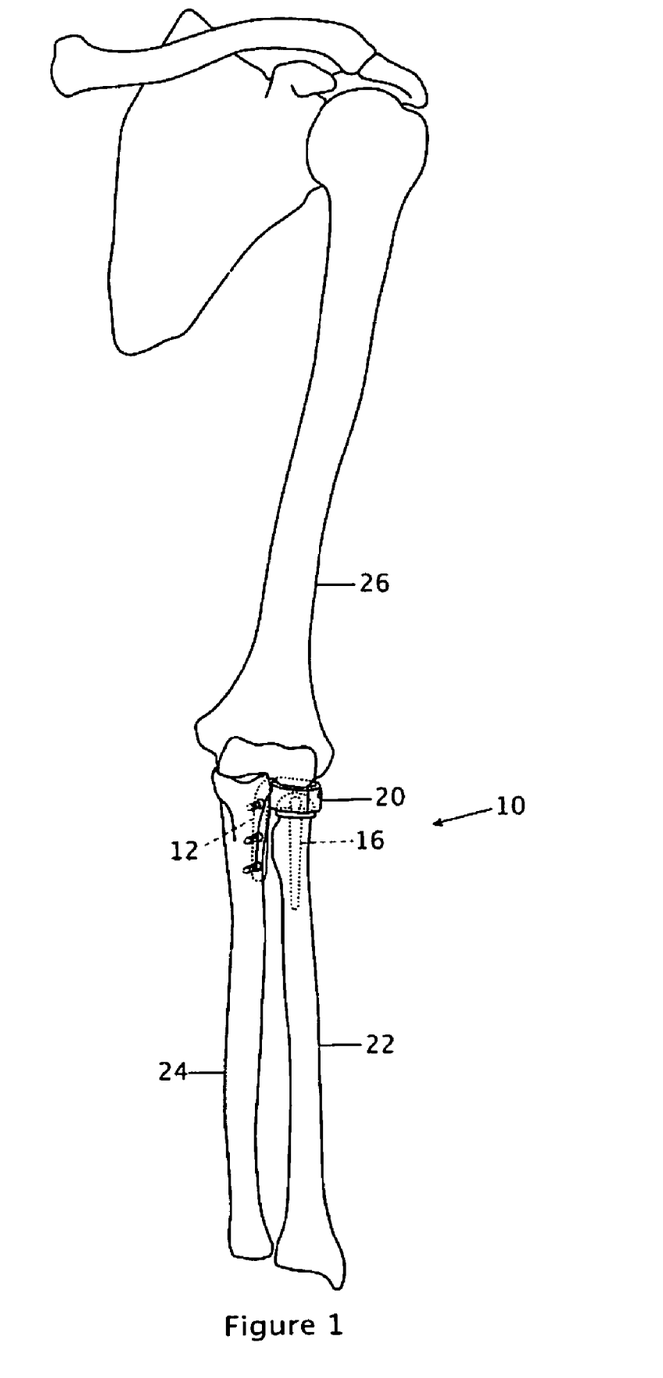
FIG. 1 is a front view of one embodiment of a proximal radioulnar joint prosthesis made in accordance with the present invention, installed on a human skeleton.

The present invention relates to an elbow or proximal radioulnar joint prosthesis. The elbow joint includes three bones—the humerus, which extends from the shoulder to the elbow, and the radius and ulna, which lie parallel to each other and form the forearm, which extends from the elbow to the wrist. Currently, when the proximal head (the upper end as seen in FIG. 1) of the radius bone is damaged or destroyed, the standard procedure is to excise the damaged portion of the radius and, if deemed necessary to insert a prosthesis into the radius bone to replace the radial head. This radial head replacement relies on the annular ligament to hold the radius in position as it did prior to the procedure. If this ligament is damaged as part of the incident which caused the damage to the radial head (such as a dislocation or a fracture of the radial head), which is typical, then the prosthesis may become dislocated from the proximal ulna and or humerus and unable to transmit any axial loads from the hand, via the forearm and the elbow to the humerus. As a result, the patient is not able to transmit axial loads from the radius to the humerus.

SUMMARY

The present invention provides a proximal radioulnar joint prosthesis that gives the patient a wide range of motion and the ability to bear weight with the affected hand.

DESCRIPTION

FIGS. 1-4 show one embodiment of a proximal radioulnar joint prosthesis 10 made in accordance with the present invention. The proximal radioulnar joint prosthesis 10 includes an ulnar brace member 12, which is secured to the ulna bone 24 with a plurality of screws 14. Also included is a radial brace member 16, which includes a stem rod 46, which secures the radial brace member 16 to the radius bone by being press fit into the medullary cavity 48 of the radius bone 22. In addition to or instead of the press fit, the radial brace member 16 may be cemented, adhered, or secured by other means to the radius bone 22. The radial brace member 16 is essentially a shaft, symmetrical about a central axis. A hemispherical ball 18 is mounted onto the upper or proximal end of the radial brace member 16, and the stem rod 46 extends downwardly from the ball 18. Further details of the radial brace member 16 will be described later.

Figure 2:
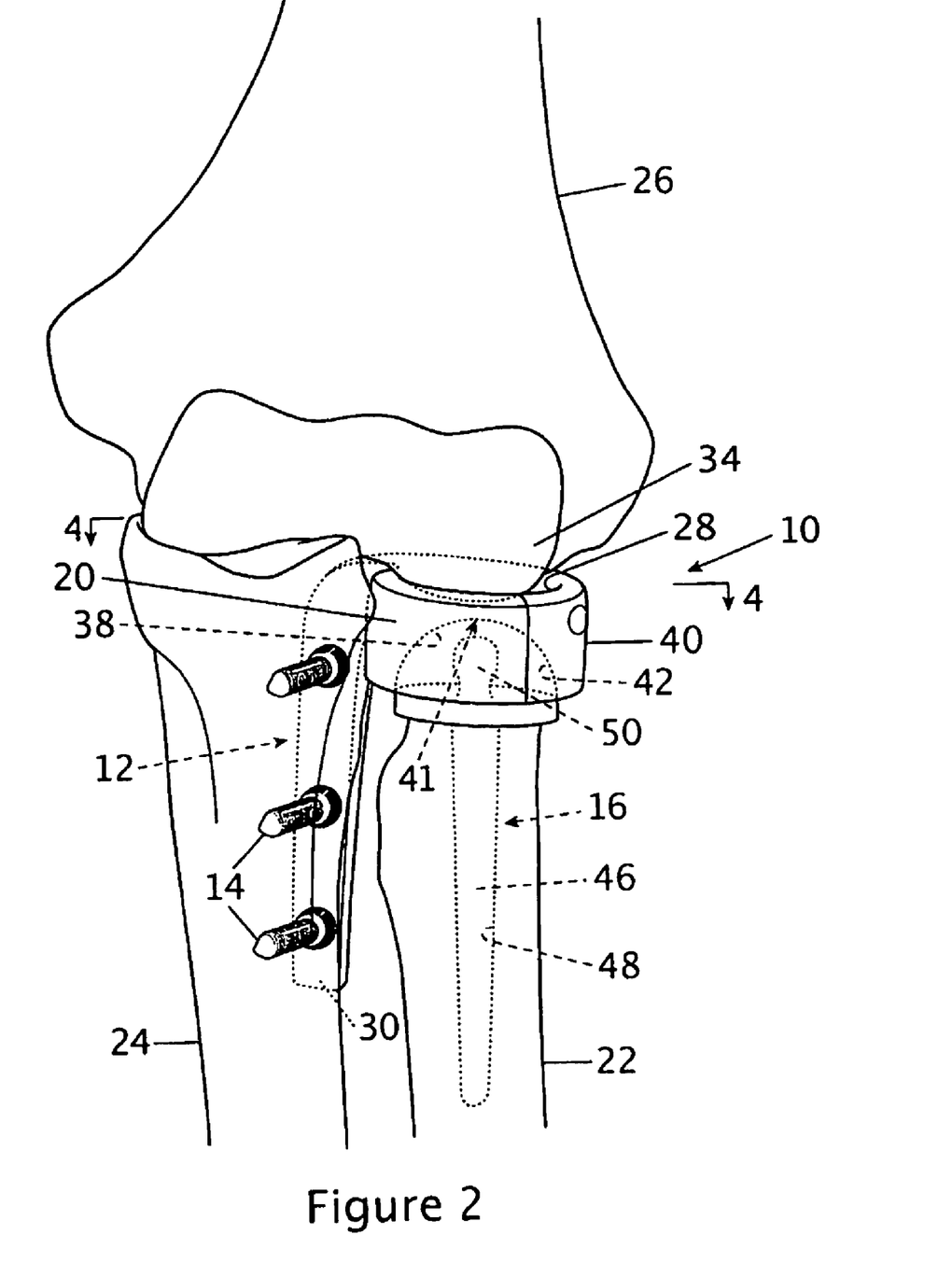
FIG. 2 is an enlarged, broken-away view of the installed proximal radioulnar joint prosthesis of FIG. 1.
Figure 3:
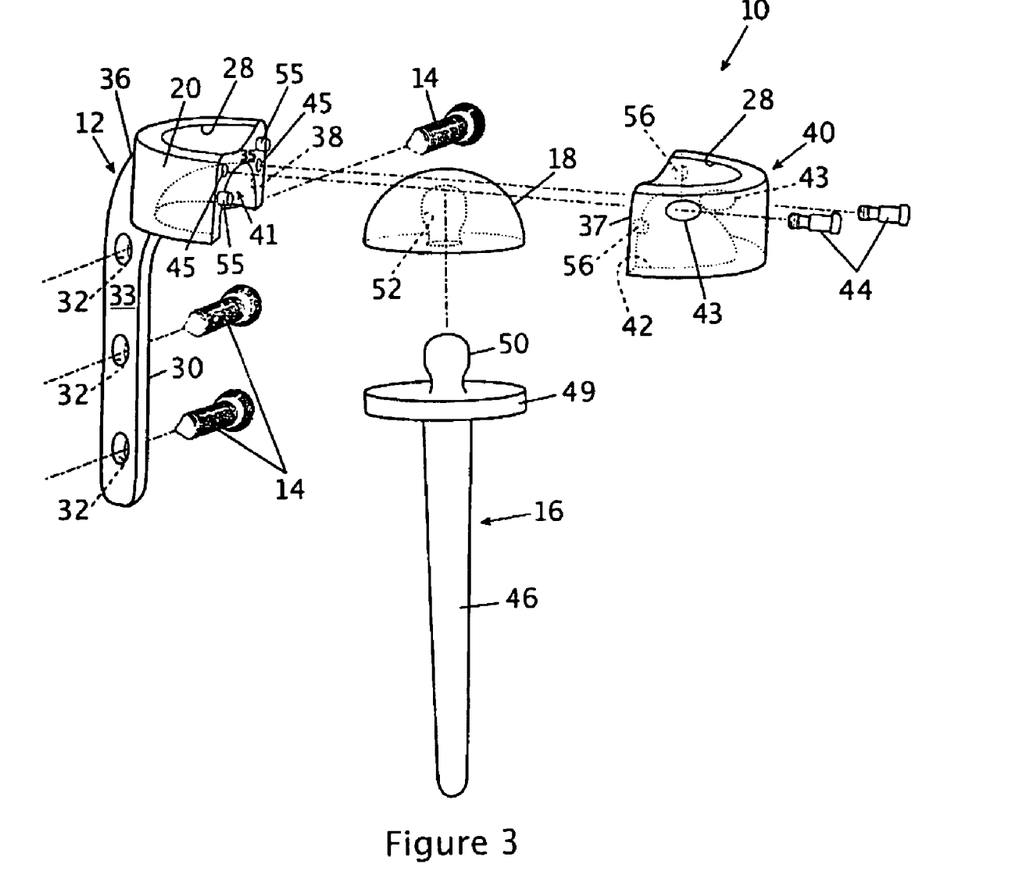
FIG. 3 is an exploded perspective view of the proximal radioulnar joint prosthesis of FIG. 2.
Figure 4:
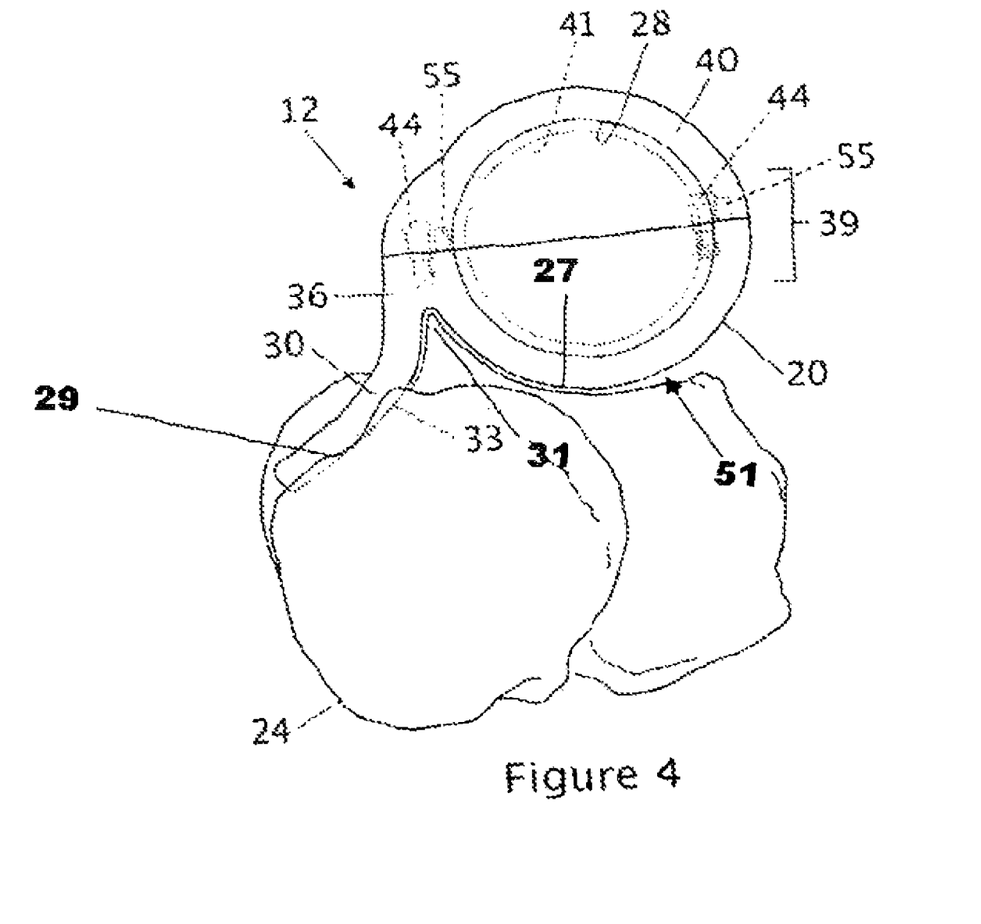
FIG. 4 is a view taken along the line 4-4 of FIG. 2.

Referring to FIGS. 2, 3 and 4 the ulnar brace member 12 includes an elongated portion 30, which lies adjacent to the ulna 24 and which is secured to the ulna 24 by means of screws 14 that extend through openings 32 in the elongated portion 30. The elongated portion 30 is substantially flat, and its face 33 that lies adjacent to the ulna 24 is generally shaped to conform to the surface of the ulna 24 in an area of the ulna 24 which is relatively flat and substantially free of important ligaments and tendons.

As shown in FIGS. 1 and 2, the elongated portion 30 of the ulnar brace member 12 is secured to the outer surface of the side of the ulna 24. Securing the ulnar brace member 12 to the side of the ulna 24 means that the ulna 24 does not have to be excised in order to install the ulnar brace member 12. Thus if the ulna 24 has not been damaged, the ulnar brace member 12 can be installed without significantly modifying the length or structure of the ulna 24. With this design, if the radial head of the radius 22 has been damaged and needs to be replaced, the ulnar brace member can be installed to retain the replacement radial head without altering or disturbing the natural interaction between the ulna and the humerus.

Securing the ulnar brace member to the side of the ulna also means that the ulnar brace member is secured to dense or compact bone tissue, providing a strong base against which to attach the prosthesis. Ideally, the screws 14 that secure the ulnar brace member 12 to the ulna 24 extend completely through the ulna 24, thereby providing a very secure attachment.

The upper or proximal end 36 of the ulnar brace member 12 includes a projection 39 (See FIG. 4), which is made up of a base 20, which is integral with the elongated portion 30, and a separate base cover 40, which is secured to the base 20 by means of self-locking bolts 44. The base 20 and base cover 40 together define a downwardly opening curved recess 41, which conforms to the shape of the ball 18 and receives the ball 18 with a close fit, providing a bearing surface that supports the ball 18 at the end of the radius bone 22, thereby serving as a curved radius-bone guide surface.

As shown best in FIGS. 2 and 4, the elongated portion 30 of the ulnar brace member 12 conforms to the shape of the rear surface portion 29 of the ulna 24 below the proximal radial notch 27, and the screws 14 tighten the elongated portion 30 of the ulnar brace member 12 against that rear surface portion 29 of the ulna 24. The ulnar brace member 12 also defines a recess 31, which wraps around the rear edge of the proximal radial notch 27, which allows the curved outer surface portion 51 of the projection 39 to fit into and conform to the shape of the proximal radial notch 27 of the ulna 24 while leaving the proximal ulna intact.

The curved surface 38 in the base 20 defines half of the curved recess 41, and the curved surface 42 in the base cover 40 defines the other half of the curved recess 41. The cover 40 and base 20 terminate in vertical planar surfaces 35, 37, which abut each other when the cover 40 is secured to the base 20 by means of the self-locking bolts 44, which extend through openings 43 in the cover 40 and are anchored in threaded openings 45 in the base 20. The base 20 also includes rounded projections 55 which mate with rounded openings 56 in the cover 40. The projections 55 and openings 56 help align the cover 40 with the base 20 prior to threading in the bolts 44. When the cover 40 and base 20 are secured together, they form a cap, including a ring, which is part of a downwardly opening curved recess 41, which receives and surrounds the ball 18 at the upper end of the radial brace 16. The recess 41 provides a bearing surface, and the ball 18 is free to swivel and slide within that bearing surface 41, in order to support the radius 22 for rotation relative to the ulna 24. Since the ring portion of the recess 41 surrounds the ball 18, it also serves to retain the ball 18 in position relative to the ulnar brace 12.

Once assembled, the cap formed by the base 20 and cover 40 also defines a shallow, upwardly opening curved recess 28 at the upper or proximal end of the ulnar brace member 12. This upwardly opening recess 28 is axially aligned with the downwardly opening recess 41, and it has a rounded or curved shape which conforms to the shape of and receives the capitellum 34. The capitellum 34 is the rounded protuberance at the distal (or lower) end of the humerus 26 that articulates with the radius 22. The recess 28 acts not only to receive the capitellum 34, but also to mechanically guide and cradle the capitellum 34 to keep it (and the humerus) in alignment with the prosthesis 10. This arrangement provides means for transmitting axial loads from the radius to the humerus by the ball 18 at the end of the radius pressing against the downwardly opening recess 41, and the upwardly opening recess 28 pressing against the humerus 26.

Looking in more detail at the radial brace 16, at the proximal end of the radial stem rod 46 are a flange 49 and a tear-shaped projection 50 axially aligned with the longitudinal axis of the radial stem rod 46. The tear-shaped projection 50 is received in a corresponding tear-shaped cavity 52 in the hemispherical ball 18 with a snap-fit, and the flat bottom surface 53 of the ball 18 abuts the top surface of the flange 49. In this embodiment, the radial stem rod 46 extends from the center of the flange 49, and the central axis of the radial stem rod 46 is aligned with the central axis of the hemispherical ball 18 and the central axis of the tear-shaped projection 50.

Figure 3A:
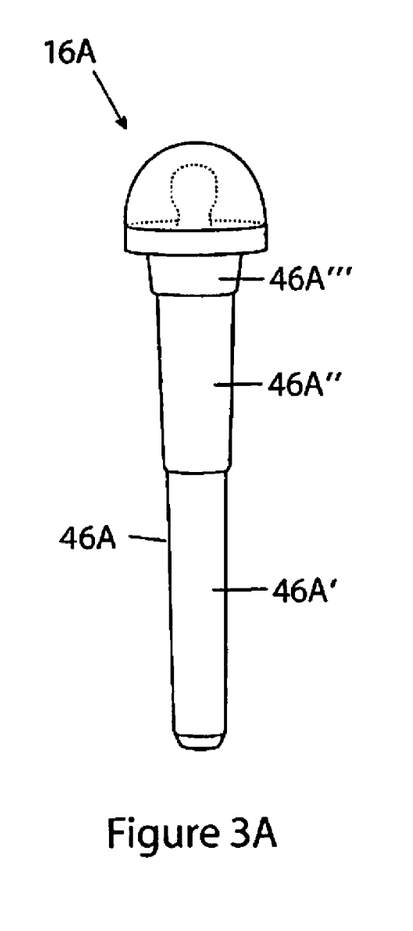
FIG. 3A is a front view of an alternative radial stem that may be used in the proximal radioulnar joint prosthesis of FIG. 1.

FIG. 3A is a view of another example of a radial brace 16A, including a radial stem rod 46A. This radial brace 16A can be used as an alternative to the radial brace 16 shown in FIG. 3. This stem rod 46A includes a lower, constant diameter section 46A', a middle tapered section 46A'', and a top tapered section 46A'''. The taper angle of the top tapered section 46A''' is greater than the taper angle of the middle tapered section 46A''. Thus, there is an untapered section 46A', a first tapered section 46A'', and a second tapered section 46A'''. Like the other radial stem, this stem 46A is designed for insertion into the medullary cavity of the radius bone (similar to FIGS. 1 and 2).

Figure 3B:
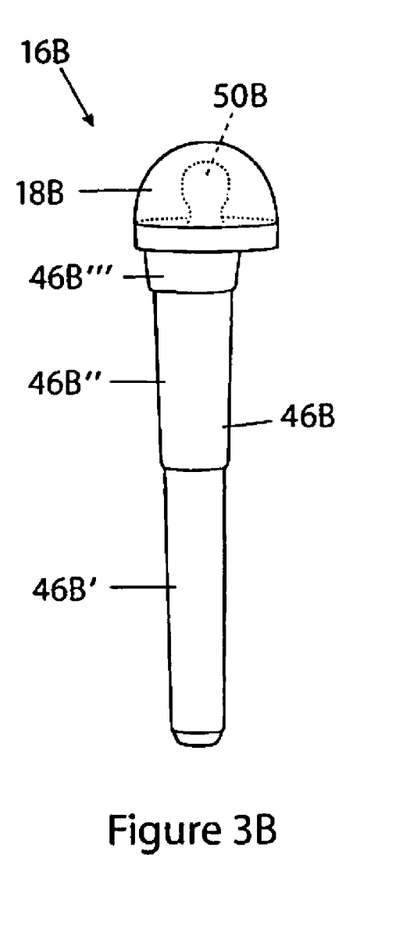
FIG. 3B a front view of still another alternative radial stem that may be used in the proximal radioulnar joint prosthesis of FIG. 1.

FIG. 3B is a view of still another example of a radial brace 16B, including a stem rod 46B, and again this radial brace 16B can be used as an alternative to the radial brace 16. Like the previous example, this radial stem 46B also has a lower, constant diameter section 46B', a middle tapered section 46B'', and a top tapered section 46B'''. However, this radial stem rod 46A has an axis that is slightly offset from the central axis of the tear-shaped projection 50B and from the central axis of the ball 18B. Offsetting the stem may be desired in order to more closely approximate the natural relative positions of the radial head and the shaft of the radius bone.

Figure 3C:
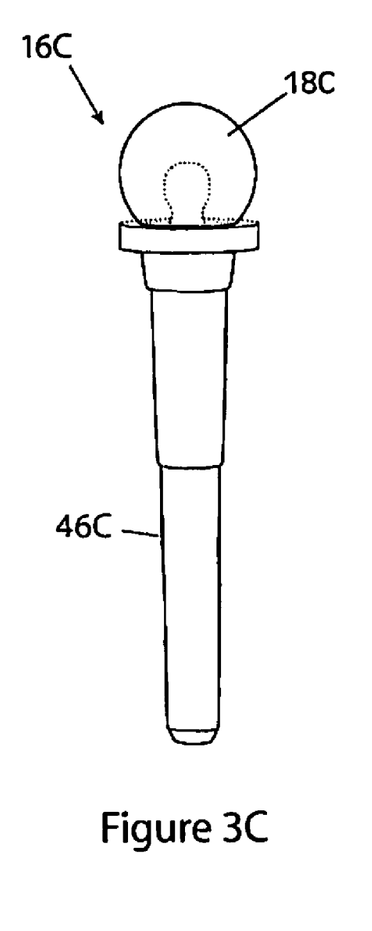
FIG. 3C is a front view of still another alternative radial stem that may be used in the proximal radioulnar joint prosthesis of FIG. 1.

FIG. 3C is a view of still another example of a radial brace 16C, including a stem rod 46C and a ball 18C. In this case, the ball 18C is more than a hemisphere. However, it has the same radius of curvature as the hemispherical ball 18 and thus is received in the same recess 41 as the hemispherical ball 18.

As indicated above, the ball 18 is able to pivotably rotate and slide within the downwardly opening recess 41 formed by the base 20 and the base cover 40. Since the ball 18 of the radial brace 16 is received in the downwardly opening recess 41 of the ulnar brace 12, which is secured to the ulna 24, and the capitellum 34 of the humerus 26 is received in the upwardly opening recess 28 of the ulnar brace 12, the radius 22 is thereby stabilized relative to the ulna 24 and the humerus 26.

In this particular embodiment 10, the metal components of the prosthesis 10 are made from cobalt chromium. Of course, other materials may alternatively be used. The metal components include the brace members 12 and 16, including the base 20 and base cover 40, the securing screws 14 and bolts 44, and the flange 49 and tear-shaped projection 50 on the brace member 16. The non-metal components are made from an ultra-high molecular weight polymer, such as UHMW polyethylene. These non-metal components include the ball 18.

To assemble and install the proximal radioulnar joint prosthesis 10, first the damaged portion of the proximal head of the radius bone 22, if present, is excised and readied for receipt of the radial brace member 16. The radial stem rod 46 of the radial brace member 16 is pressed into the medullary cavity of the radius 22. The radial stem rod 46 may be cemented or adhered in place, if desired. Then the ball 18 is snapped onto the tear-shaped projection 50 to assemble the ball 18 onto the radial brace 16. Alternatively, the ball 18 could be snapped onto the radial brace 16 before the radial brace 16 is inserted into the medullary cavity of the radius 22. However, if the radial brace 16 is inserted into the bone before the ball 18 is mounted to the stem, a tool (not shown) may be used, acting against the flange 49 or against the projection 50, to "hammer" the stem rod 46 into the medullary cavity 48 of the radius 22 prior to snapping the ball 18 onto the projection 50. Then, holes are drilled into the ulna bone 24, and the ulnar brace member 12 is mounted, via self-locking screws 14, onto the upper portion of the ulna 24, as shown, with the elongated portion 30 of the ulnar brace member 12 in contact with the ulna 24. Alternatively, compression screws, pegs or other means of fixation may be used in place of the self-locking screws 14. In addition, a template may be used to determine where the holes are to be drilled.

As is best appreciated in FIGS. 3 and 4, the elongated portion 30 of the ulnar brace member 12 extends downwardly from the base 20 and is substantially tangent to the base 20. This orientation allows the mounting of the elongated portion 30 onto a relatively flat area of the proximal ulna 24, where no important ligaments or muscle connections are located, while the downwardly opening recess 41 is axially aligned with the radial head 18 of the radius 22, and the upwardly opening recess 28 is axially aligned with the capitellum 34 of the humerus 26.

With the cover 40 removed, the radius 22 is moved toward the ulna 24 until the ball 18 (which serves as a prosthesis for the radial head) of the radial brace member 16 is inserted into the partial cavity 38 of the base 20. The base cover 40 is then installed onto the base 20 with the bolts 44 so as to "capture" the ball 18 within the downwardly opening recess 41. The ball 18 is able to rotate and slide within the cavity 42, which is fixed relative to the ulna 24. This stabilizes the radius 22 relative to the ulna 24. The overall length of the radius 22, together with the radial brace member 16, is such that the ball 18 is trapped within the recess 41, and it is unlikely to "pop" out or otherwise become dislocated as the radius 22 rotates relative to the ulna 24 and as the elbow joint is flexed. The upwardly opening curved recess 28 receives the capitellum 34 of the distal humerus 26, as explained earlier. There generally is a slight space or gap between the capitellum 34 and the recess 28, so they do not come into contact until the person bears weight, at which point the capitellum 34 comes into contact with the recess 28, thereby providing support for the weight.

While the embodiment described above shows a simple means for rotationally securing the ball 18 of the radial brace member 16 to the ulnar brace member 12, various other mounting mechanisms could be used to achieve this result. For instance, the entire projection 39 containing the downwardly opening recess 41 could hinge up or out of the way far enough for the ball 18 to clear the edge of the recess and then could hinge downwardly and be fixed in the downward position to retain the ball 18 in the recess 41. Alternatively, the body that forms the downwardly opening recess and upwardly opening recess could be a separate piece from the ulnar brace member 12, designed to be placed over the ball 18 and then to be fixed relative to the ulnar brace member 12 by means such as snapping or bolting. Similarly, the ulnar brace member 12 could be secured to the outer surface of the ulna 24 by other means, such as by being adhered to the ulna 24.

Figure 5:
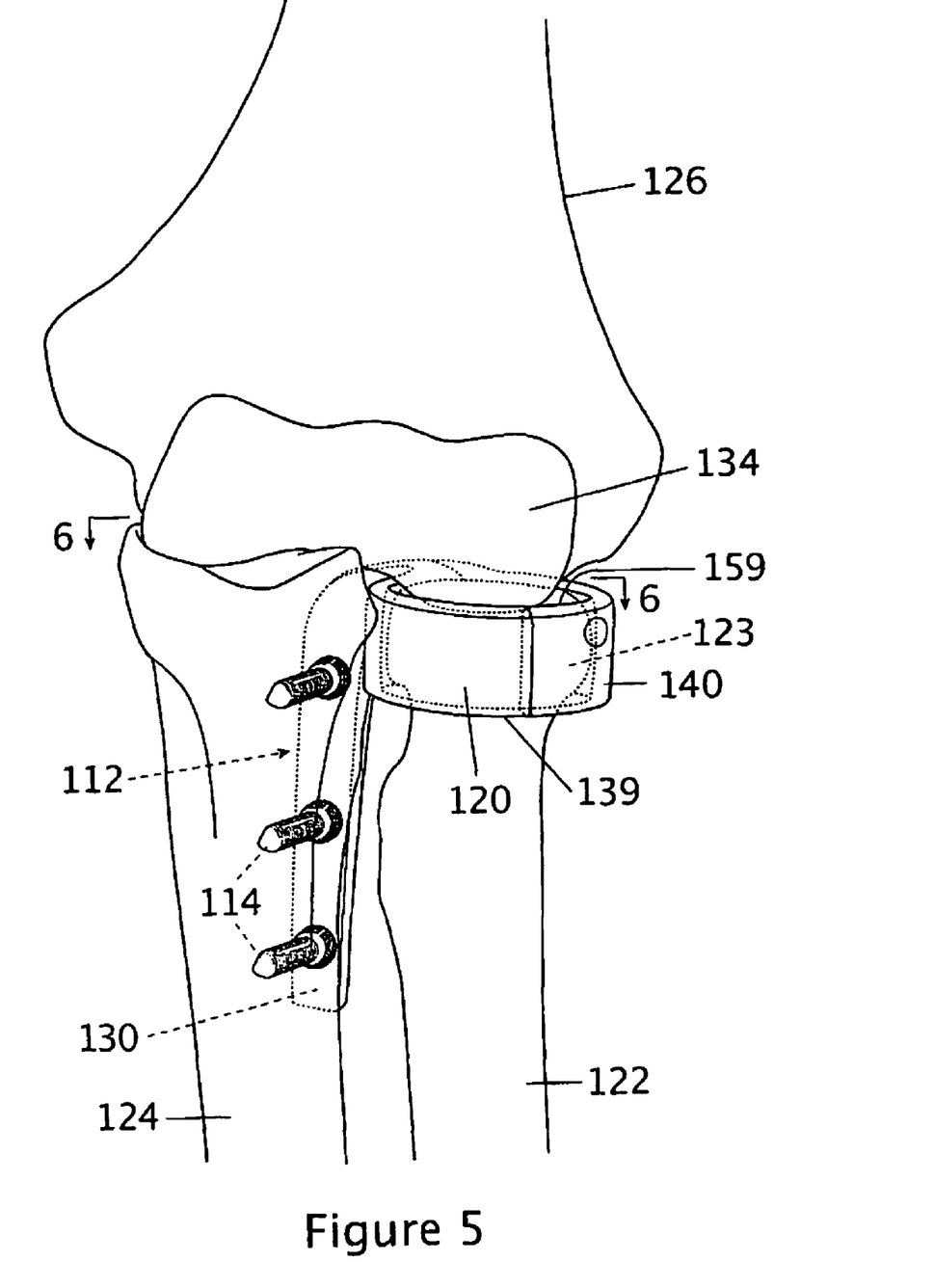
FIG. 5 is a front view of a second embodiment of a proximal radioulnar joint prosthesis made in accordance with the present invention, installed on a human skeleton.
Figure 6:
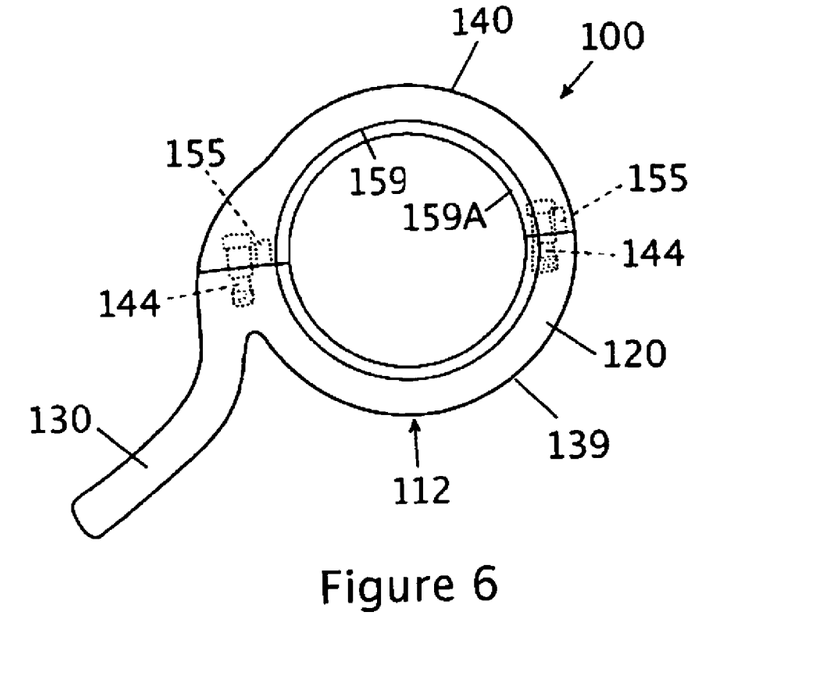
FIG. 6 is a view taken along the line 6-6 of FIG. 5 with the bone removed for clarity.

FIGS. 5 and 6 show another embodiment of a proximal radioulnar joint prosthesis 100 made in accordance with the present invention. As in the previous embodiment, this embodiment includes an ulnar brace member 112 having an elongated portion 130, which conforms to the outer surface of the ulna bone 124 and is secured to the ulna bone 124 via screws 114. The ulnar brace member 112 again includes a base portion 120 and a cover 140. The base 120 includes rounded projections 155 (shown in FIG. 6) to aid in aligning the cover 140 and the base 120, and the cover 140 is secured to the base 120 with bolts 144. In this embodiment, the base 120 and cover 140 collectively form a ring 139 that defines an opening 159. As in the first embodiment, the ring 139 has an inside diameter that is slightly larger than the outside diameter of the radial head 123 of the radius bone 122, and the ring 139 encircles the radial head 123, as shown in FIG. 5. The inner surface of the ring 139 retains the radial head 123 of the radius bone 122 and provides a bearing surface that rotationally supports the radius bone 122, serving as a curved radius-bone guide surface. The opening 159 allows contact between the radial head 123 and the capitellum 134, thereby preserving the natural interaction between the radial head 123 and the capitellum 134, in which the axial load on the radius 122 is transmitted to the humerus by contact between the radius and the humerus. By guiding the radial head 123, keeping it aligned with the capitellum 134 of the humerus, and allowing the humerus to contact the radius 122, the ring 139 provides means for transmitting axial loads from the radius 122 to the humerus. The ring 139 of this embodiment is similar to the projection 39 of the previous embodiment, except it is open instead of being closed, where the cap of the previous embodiment defines the closed upper surface 28, which receives the capitellum 134 and the downwardly opening recess 41, which receives the radial head 18 of the radius bone 22.

In this embodiment, the ring 139 is lined with a polymeric liner 159A, such as UHMW polyethylene, which is the material that comes into contact with and provides the bearing surface for the radius bone 122. Of course, in other embodiments, the liner may be made of another suitable material or may be omitted altogether. As with the first embodiment, the ring 139 holds the radius 122 in position relative to the ulna 124, thereby performing a function similar to that of the natural annular ligament, which may have been damaged. In this embodiment, there is no radial brace member.

However, in addition to being used with a healthy, undamaged radius bone 122 as shown in FIG. 5, this embodiment of the proximal radioulnar joint prosthesis 100 could also be used with a variety of artificial radial head replacements, such as the radial brace members 16, 16A, 16B described earlier, or others. When replacing the radial head, the proximal radioulnar joint prosthesis 100 can be used by securing the ulnar brace member 112 to the ulna 124, and then securing the cover 140 to the base 120 to encircle the particular radial head replacement being used. Thus the prosthesis 100 provides the ability to retain and rotationally support the radius bone 122 for a variety of radial heads, both natural and prosthetic.

In addition, the ring of the proximal radioulnar joint prosthesis could be positioned in a slightly more distal direction. That is, the ring could encircle the radius bone below the radial head, instead of encircling the radial head.

Figure 7:
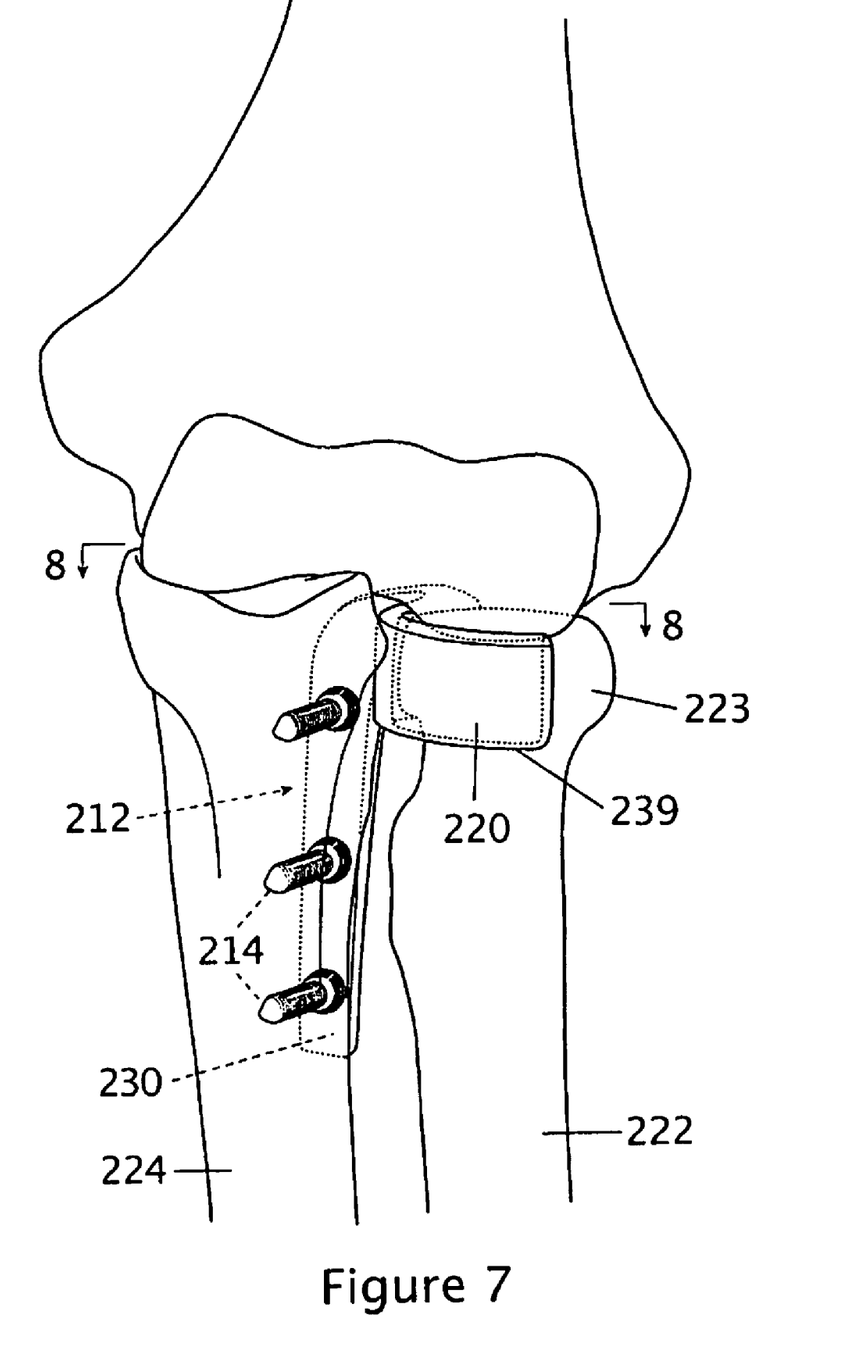
FIG. 7 is a front view of a third embodiment of a proximal radioulnar joint prosthesis made in accordance with the present invention, installed on a human skeleton.
Figure 8:
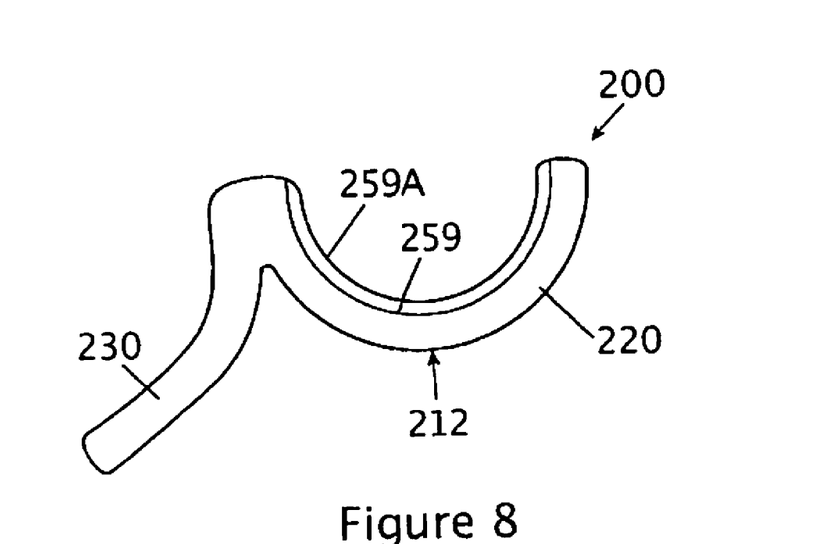
FIG. 8 is a view taken along the line 8-8 of FIG. 7, with the bone removed for clarity.

FIGS. 7 and 8 show another embodiment of a proximal radioulnar joint prosthesis 200 made in accordance with the present invention. Like the previous embodiments, this ulnar brace member 212 includes an elongated portion 230, which conforms to the outer surface of the ulna bone 224. In this embodiment, the base 220 of the prosthesis 200 defines a partial-ring 259, which provides the bearing surface that supports the radial head 223 of the radius bone 222, thereby serving as a curved radius-bone guide surface, but it has no cover or other means for completely encircling the proximal end of the radius bone 222. In this case, the partial ring 259 is a half-ring, so it is very similar to the embodiment of FIG. 6 with the cover 140 removed. As in the previous embodiment, the partial ring 259 allows contact between the radial head 223 and the capitellum, thereby preserving the natural interaction between the radial head 223 and the capitellum, in which the axial load on the radius 222 is transmitted to the humerus by contact between the radius and the humerus. By guiding the radial head 223, keeping it aligned with the capitellum of the humerus, and allowing the humerus to contact the radius 222, the partial ring 259 provides means for transmitting axial loads from the radius 222 to the humerus. This prosthesis 200 is not designed to replicate the retaining function of the annular ligament, but it is designed to provide a bearing surface for supporting the radial head 223 of a radius bone as it articulates relative to the ulna 224. Similar to the previous embodiment, the partial ring 259 is lined with a polymeric liner 259A, which provides the actual bearing surface against which the radial head 223 slides. This prosthesis 200 may be used with the natural radial head 223 of the radius bone as shown in FIG. 7 or with an artificial replacement for the radial head. This prosthesis 200 is secured to the outer surface of the ulna bone 224 with screws 214 in the same manner as described for the previous embodiments.

While some embodiments of the present invention have been described above, it will be obvious to those skilled in the art that various modifications may be made to these embodiments without departing from the scope of the present invention as claimed.

What is claimed is:

1. A proximal radioulnar joint prosthesis, comprising:
an ulnar brace member having an upper end and a lower end, and including a substantially flat, downwardly-extending elongated portion defining an elongated abutment surface having a shape which conforms to the outer surface of the ulna bone near its proximal end;
said ulnar brace member including a projection from said downwardly-extending elongated portion and defining a recess between the projection and the downwardly-extending elongated portion; wherein said projection has a curved outer surface portion and defines a curved radius-bone guide surface fixed relative to said elongated portion and positioned to be aligned with and to receive and support the proximal end of the radius bone for rotation relative to the ulnar brace member when the elongated portion is abutting and mounted on the proximal end of the ulna bone; means for mounting said ulnar brace member on a human ulna near the proximal end of the ulna such that the recess will receive the rear edge of the proximal radial notch of the ulna and the curved outer surface portion of the projection will fit into the proximal radial notch of the ulna while leaving the proximal ulna intact; and said ulnar brace member further including means for transmitting axial loads from the radius to the humerus.

2. A proximal radioulnar joint prosthesis, comprising:
an ulnar brace member having an upper end and a lower end, and including a substantially flat, downwardly-extending elongated portion defining an elongated abutment surface having a shape which conforms to the outer surface of the ulna bone near its proximal end;
said ulnar brace member defining a curved radius-bone guide surface fixed relative to said elongated portion and positioned to be aligned with and to receive and support the proximal end of the radius bone for rotation relative to the ulnar brace member when the elongated portion is abutting and mounted on the proximal end of the ulna bone; and said ulnar brace member further including means for transmitting axial loads from the radius to the humerus;
wherein the curved radius bone guide surface is part of at least a partial ring which is positioned to at least partially encircle the proximal end of the radius when the ulnar brace member is mounted on the proximal end of the ulna bone.

3. A proximal radioulnar joint prosthesis as recited in claim 2, wherein the means for transmitting axial loads from the radius to the humerus includes said curved radius bone guide surface defining an opening through which the radial head may extend to contact the capitellum.

4. A proximal radioulnar joint prosthesis as recited in claim 2, wherein the means for transmitting axial loads from the radius to the humerus includes a cap, having an upwardly opening concave surface for receiving and supporting the capitellum and a downwardly opening concave surface for receiving and supporting the proximal radial head.

5. A proximal radioulnar joint prosthesis as recited in claim 3, wherein the at least partial ring is a complete ring and includes a base, which is integral with the elongated portion and forms part of the ring; and a cover, which mates with the base to complete the ring.

6. A proximal radioulnar joint prosthesis as recited in claim 4, wherein the at least partial ring is a complete ring and includes a base, which is integral with the elongated portion and forms part of the ring and part of the cap; and a cover, which mates with the base to complete the ring and the cap.

7. A proximal radioulnar joint prosthesis as recited in claim 6, wherein said elongated portion defines lateral through holes for use in securing the ulnar brace member to the ulna bone.

8. A proximal radioulnar joint prosthesis as recited in claim 1, and further comprising a radial brace member including a rod defining a longitudinal axis and distal and proximal ends; and a ball at the proximal end of said rod which serves as the radial head of the radius bone, wherein said radius bone guide surface conforms to the shape of said ball.

9. A proximal radioulnar joint prosthesis as recited in claim 4, and further comprising a radial brace member including a rod defining a longitudinal axis and distal and proximal ends; and a ball at the proximal end of said rod, said rod and ball being sized and shaped such that the rod can be inserted into the medullary cavity of the radius bone, in order to cause the ball to replace and become the radial head of the radius bone, wherein said downwardly opening concave surface conforms to the shape of said ball and the ulnar and radial brace members are sized and shaped such that, when the radial brace member will be mounted on the radius bone with the rod inserted into the medullary cavity of the radius bone, and the ulnar brace member will be installed on the ulna bone, the downwardly opening concave surface of the ulnar brace member will at least partially encircle the ball and will thereby at least partially encircle the proximal end of the radius.

10. A proximal radioulnar joint prosthesis as recited in claim 9, wherein said ball defines a central axis, and the longitudinal axis of the rod of said radial brace member is offset from the central axis of said ball.

11. A proximal radioulnar joint prosthesis as recited in claim 10, wherein the at least partial ring is a complete ring and includes a base, which is integral with the elongated portion and forms part of the ring and part of the cap; and a cover, which mates with the base to complete the ring and the cap; and wherein said elongated portion defines lateral through holes for use in securing the ulnar brace member to the ulna bone.

12. A method of installing a proximal radioulnar joint prosthesis, comprising the steps of:
fixing an ulnar brace to the outer surface of the ulna bone of a patient near the proximal end of the ulna bone; and
aligning said ulnar brace with the patient's radius bone so that the ulnar brace provides a bearing surface that supports the patient's radius bone;
wherein said ulnar brace includes a base member and a cover, and including the step of assembling said cover and base member together to form a ring which encircles the radius bone adjacent its proximal end.

13. A method of installing a proximal radioulnar joint prosthesis as recited in claim 12, and further comprising the step of:
inserting a radial brace member into the medullary cavity of the radius bone, said radial brace member including:
a rod, defining a longitudinal axis and distal and proximal ends; and
a radial head prosthesis at the proximal end of said rod, wherein, upon insertion of the rod into the medullary cavity of the radius bone, the radial head prosthesis becomes the head of the radius bone which is encircled by said ring;
wherein said bearing surface supports said radial head prosthesis.

14. A method of installing a proximal radioulnar joint prosthesis as recited in claim 13, wherein said ulnar brace member includes a cap which defines said ring, said cap also defining an upwardly opening concave surface which cradles the capitellum and a downwardly opening recess, said recess receiving said radial head prosthesis.

* * * * *